US00PP19202P2

(12) United States Plant Patent
Michalik

(10) Patent No.: US PP19,202 P2
(45) Date of Patent: Sep. 9, 2008

(54) ***GERANIUM* PLANT NAMED 'PACMAR'**

(50) Latin Name: *Pelargonium×hortorum*
Varietal Denomination: Pacmar

(75) Inventor: Andrea Michalik, Dresden (DE)

(73) Assignee: Elsner PAC Jungpflanzen, Dresden (DE)

( * ) Notice: Subject to any disclaimer, the term of this patent is extended or adjusted under 35 U.S.C. 154(b) by 0 days.

(21) Appl. No.: 11/809,918

(22) Filed: Jun. 1, 2007

(51) Int. Cl.
*A01H 5/00* (2006.01)

(52) U.S. Cl. ..... Plt./329
(58) Field of Classification Search ..... Plt./329
See application file for complete search history.

*Primary Examiner*—Kent L Bell
(74) *Attorney, Agent, or Firm*—C. A. Whealy

(57) ABSTRACT

A new and distinct cultivar of Zonal *Geranium* plant named 'Pacmar', characterized by its upright and rounded plant habit; freely branching habit; moderately vigorous growth habit; dark green-colored leaves; freely flowering habit; semi-double bright red purple-colored flowers; and good garden performance.

1 Drawing Sheet

Botanical designation: *Pelargonium×hortorum.*
Cultivar denomination: 'PACMAR'.

BACKGROUND OF THE INVENTION

The present invention relates to a new and distinct cultivar of Zonal *Geranium*, botanically known as *Pelargonium×hortorum,* and hereinafter referred to by the name 'Pacmar'.

The new Zonal *Geranium* is a product of a planned breeding program conducted by the Inventor in Dresden, Germany. The objective of the breeding program is to create new Zonal *Geranium* cultivars with dark green-colored foliage and attractive flower coloration.

The new Zonal *Geranium* originated from a cross-pollination made by the Inventor in Dresden, Germany during the summer of 2002 of two unnamed proprietary selections of *Pelargonium×hortorum,* not patented. The cultivar Pacmar was discovered and selected by the Inventor as a flowering plant from within the progeny of the stated cross-pollination in a controlled environment in Dresden, Germany in June, 2003.

Asexual reproduction of the new Zonal *Geranium* by vegetative terminal cuttings in a controlled environment in Dresden, Germany since December, 2003, has shown that the unique features of this new Zonal *Germanium* are stable and reproduced true to type in successive generations.

SUMMARY OF THE INVENTION

The cultivar Pacmar has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Pacmar'. These characteristics in combination distinguish 'Pacmar' as a new and distinct cultivar of Zonal *Geranium:*

1. Upright and rounded plant habit.
2. Freely branching habit.
3. Moderately vigorous growth habit.

4. Dark green-colored leaves.
5. Freely flowering habit.
6. Semi-double bright red purple-colored flowers.
7. Good garden performance.

Plants of the new Zonal *Geranium* differ primarily from plants of the parent selections in plant vigor and flower color.

Plants of the new Zonal *Geranium* can be compared to plants of the *Pelargonium×hortorum* cultivar Pacfox, disclosed in U.S. Plant Pat. No. 18,374. In side-by-side comparisons conducted in Dresden, Germany, plants of the new Zonal *Geranium* differed from plants of the cultivar Pacfox in the following characteristics:

1. Plants of the new Zonal *Geranium* were not as freely branching as plants of the cultivar Pacfox.
2. Leaves of plants of the new Zonal *Geranium* were darker green in color than leaves of plants of the cultivar Pacfox.
3. Leaves of plants of the new Zonal *Geranium* did not have a distinct zonation pattern whereas leaves of plants of the cultivar Pacfox had a distinct zonation pattern.
4. Plants of the new Zonal *Geranium* and the cultivar Pacfox differed slightly in flower color.

BRIEF DESCRIPTION OF THE PHOTOGRAPH

The accompanying colored photograph illustrates the overall appearance of the new Zonal *Geranium*, showing the colors as true as it is reasonably possible to obtain in colored reproductions of this type. Colors in the photograph may differ slightly from the color values cited in the detailed botanical description which accurately describe the colors of the new Zonal Geranium. The photograph comprises a side perspective view of a typical flowering plant of 'Pacmar' grown in a container.

DETAILED BOTANICAL DESCRIPTION

The aforementioned photograph and following observations, measurements and values describe plants grown in Dresden, Germany in a glass-covered greenhouse during the autumn and winter and under conditions which closely approximate commercial *Geranium* production. During the production of the plants, day temperatures averaged 18° C., night temperatures averaged 16° C. and light levels ranged from 15 kilolux to 100 kilolux. Plants were about four months old when the photograph was taken, and plants were about six months old when the description was taken. In the detailed description, color references are made to The Royal Horticultural Society Colour Chart, 1995 Edition, except where general terms of ordinary dictionary significance are used.

Botanical classification: *Pelargonium×hortorum* cultivar Pacmar.

Parentage:

*Female, or seed, parent.*—Unnamed proprietary selection of *Pelargonium×hortorum, not patented.*

*Male or pollen parent.*—Unnamed proprietary selection of *Pelargonium×hortorum,* not patented.

Propagation:

*Type.*—By vegetative terminal cuttings.

*Time to initiate roots, summer.*—About 18 days at temperatures of 20° C.

*Time to initiate roots, winter.*—About 22 days at temperatures of 20° C.

*Time to produce a rooted young plant, summer.*—About 25 days at temperatures of 20° C.

*Time to produce a rooted young plant, winter.*—About 30 days at temperatures of 20° C.

*Root description.*—Fine, fibrous; white in color.

*Rooting habit.*—Freely branching; dense.

Plant description:

*Plant/growth habit.*—Upright to rounded plant habit; densely foliated. Moderately vigorous growth habit. Freely basal branching habit with about five lateral branches developing per plant.

*Plant height, to top of umbels.*—About 30 cm.

*Plant height, to top of leaves.*—About 20 cm.

*Plant width.*—About 40 cm.

*Lateral branches.*—Length: About 7 cm. Diameter: About 8 mm. Internode length: About 1.5 cm. Texture: Pubescent. Color: 146B.

Foliage description:

*Arrangement.*—Alternate or opposite; simple.

*Length.*—About 4.5 cm.

*Width.*—About 8 cm.

*Shape.*—Reniform.

*Apex.*—Rounded.

*Base.*—Cordate; partly imbricate.

*Margin.*—Bi-crenate.

*Venation pattern.*—Palmate.

*Texture, upper and lower surfaces.*—Pubescent.

*Color.*—Developing foliage, upper surface: 137A. Developing foliage, lower surface: 146B. Fully expanded foliage, upper surface: 139A; venation, 146C. Fully expanded foliage, lower surface: 147B; venation, 146B. Zonation pattern: Not discernible. Petiole: Length: About 7 cm. Diameter: About 3 mm. Texture, upper and lower surfaces: Pubescent. Color, upper and lower surfaces: 164B.

Flower description:

*Flower arrangement.*—Semi-double rotate flowers arranged in rounded hemispherical umbels arising from apical leaf axils. Umbels displayed above the foliage on strong peduncles. Flowers face upright to outward; flowers mostly flat. Flowers persistent. Flowers not fragrant.

*Quantity of flowers.*—Freely flowering habit; about seven flower umbels per plant each with about 20 flower buds and open flowers.

*Flowering season.*—Year-round under greenhouse conditions. In the garden in Dresden, Germany, flowering is continuous from April until frost in the autumn.

*Flower longevity.*—Individual flowers last about six to ten days on the plant; umbels last about three to four weeks on the plant.

*Umbel height.*—About 6 cm.

*Umbel diameter.*—About 10 cm.

*Flower diameter.*—About 5 cm.

*Flower depth* (*height*).—About 2 cm.

*Flower buds.*—Length: About 7 mm. Diameter: About 7 mm. Shape: Roughly elliptic. Color: 143C.

*Petals.*—Quantity per flower: About eight. Length: About 2.5 cm. Width: About 2.7 cm. Shape: Obovate. Apex: Rounded. Base: Attenuate. Margin: Entire. Texture, upper and lower surfaces: Smooth, glabrous; velvety. Color: When opening and fully opened, upper surface: Slightly more red than 57A; towards the base, close to 155D; venation, 61B. When opening and fully opened, lower surface: Slightly more red than 57A; towards the base, close to 155D; venation, 61B.

*Petaloids.*—Quantity per flower: None to about four. Length: About 1.8 cm. Width: About 1.5 cm. Shape: Irregular. Apex: Rounded. Base: Attenuate. Margin: Entire. Texture, upper and lower surfaces: Smooth, glabrous; velvety. Color: When opening and fully opened, upper surface: Slightly more red than 57A; towards the base, close to 155D; venation, 61B. When opening and fully opened, lower surface: Slightly more red than 57A; towards the base, close to 155D; venation, 61B.

*Sepals.*—Quantity per flower: Five, arranged in a single whorl. Length: About 1.2 cm. Width: About 3 cm. Shape: Lanceolate. Apex: Acute. Margin: Entire. Texture, upper and lower surfaces: Pubescent. Color, upper surface: 46A. Color, lower surface: Towards the apex, 146B; towards the base, 46A.

*Peduncle* (*umbel stem*).—Length: About 12 cm. Diameter: About 5 mm. Strength: Strong. Angle: Mostly erect to outwardly slanted. Texture: Pubescent. Color: 152A.

*Pedicel* (*individual flower stem*).—Length: About 2.5 cm. Diameter: About 2 mm. Strength: Moderately strong; flexible. Texture: Pubescent. Color: 46A.

*Reproductive organs.*—Androecium: Stamen quantity per flower: About seven. Anther length: About 2 mm. Anther shape: Tubular. Anther color: 169C. Pollen amount: Abundant. Pollen color: 169C. Gynoecium: Pistil quantity per flower: One. Pistil length: About 1 cm. Stigma shape: Five-parted. Stigma color: 60A. Style length: About 3 mm. Style color: 60C. Ovary color: 148B.

*Seeds.*—Length: About 3 mm. Diameter: About 1 mm. Color: 165A.

Disease/pest resistance: Plants of the new Zonal *Geranium* have not been observed to be resistant to pathogens and pests common to Zonal *Geraniums.*

Garden performance: Plants of the new Zonal *Geranium* have been observed to tolerate rain, wind and temperatures ranging from about 1° C. to about 35° C. and have demonstrated good garden performance.

It is claimed:

1. A new and distinct Zonal *Geranium* plant named 'Pacmar' as illustrated and described.

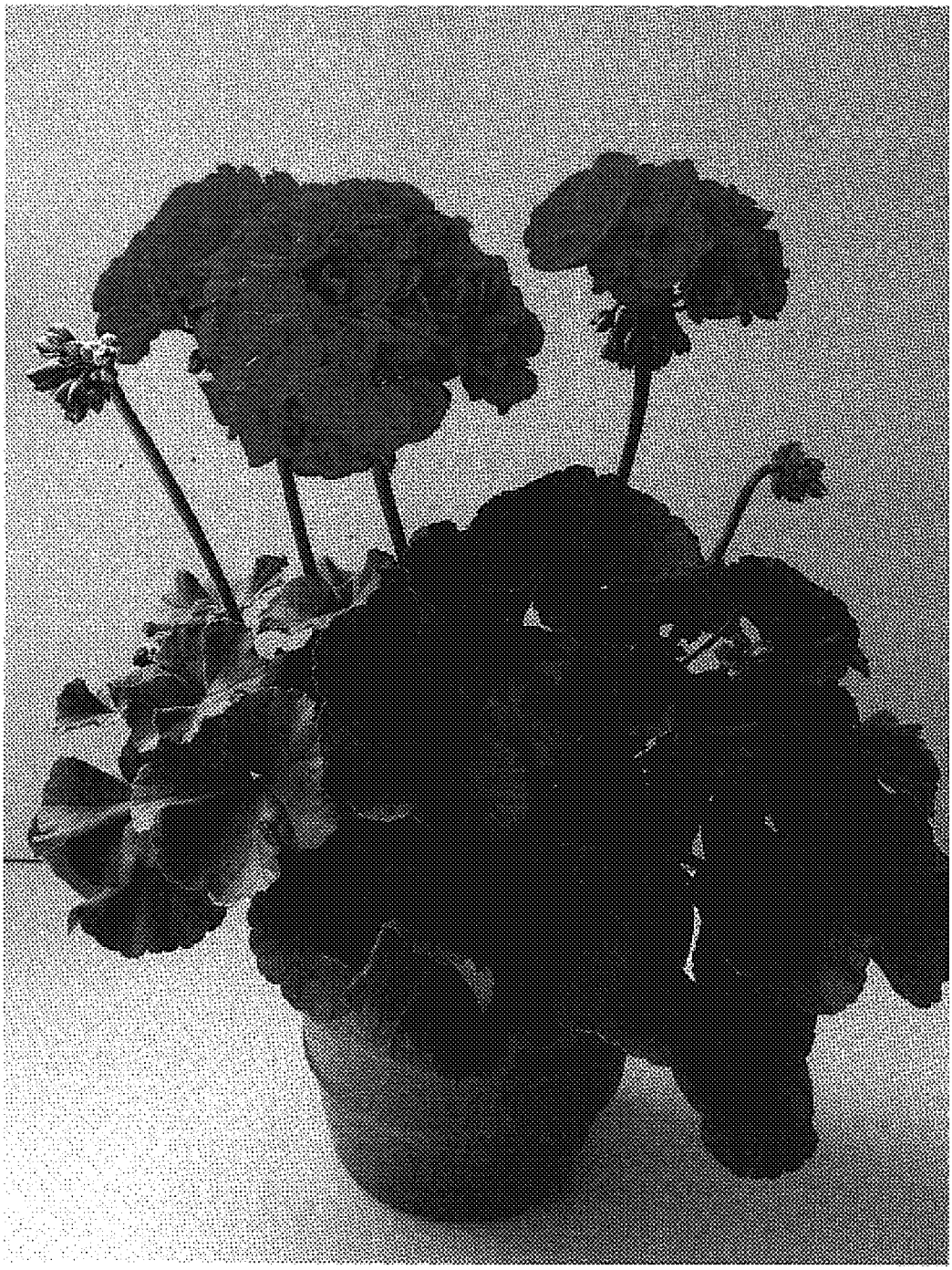

* * * * *